United States Patent
Nagy

(10) Patent No.: US 6,586,545 B1
(45) Date of Patent: Jul. 1, 2003

(54) COMPLEXES BASED ON FOUR-MEMBERED CYCLIC ANIONIC SIX-ELECTRON-DONOR LIGANDS

(75) Inventor: Sandor Nagy, Naperville, IL (US)

(73) Assignee: Equistar Chemicals, LP, Houston, TX (US)

( * ) Notice: Subject to any disclaimer, the term of this patent is extended or adjusted under 35 U.S.C. 154(b) by 32 days.

(21) Appl. No.: 10/027,143

(22) Filed: Dec. 20, 2001

(51) Int. Cl.[7] .................................................. C08F 4/44
(52) U.S. Cl. ...................... 526/161; 526/160; 526/172; 526/170; 526/134; 526/348; 502/103; 502/117; 502/208; 502/216
(58) Field of Search ................................. 526/134, 160, 526/170, 161, 172; 502/103, 117, 208, 216

(56) References Cited

U.S. PATENT DOCUMENTS

| | | | |
|---|---|---|---|
| 4,752,597 A | 6/1988 | Turner | 502/104 |
| 4,791,180 A | 12/1988 | Turner | 526/160 |
| 5,153,157 A | 10/1992 | Hlatky et al. | 502/117 |
| 5,198,401 A | 3/1993 | Turner et al. | 502/155 |
| 5,241,025 A | 8/1993 | Hlatky et al. | 526/129 |
| 5,414,180 A | 5/1995 | Geerts et al. | 585/525 |
| 5,539,124 A | 7/1996 | Etherton et al. | 548/402 |
| 5,554,775 A | 9/1996 | Krishnamurti et al. | 556/7 |
| 5,637,659 A | 6/1997 | Krishnamurti et al. | 526/133 |
| 5,637,660 A | 6/1997 | Nagy et al. | 526/160 |
| 5,648,440 A | 7/1997 | Sugano et al. | 526/132 |
| 5,902,866 A | 5/1999 | Nagy et al. | 526/133 |
| 6,211,311 B1 | 4/2001 | Wang et al. | 526/131 |
| 6,232,260 B1 | 5/2001 | Nagy et al. | 502/155 |

OTHER PUBLICATIONS

Dittmer et al. J. Org. Chem. 1972, 37, 1111–1115.*
Power, T. D.; Sebastian, J. F. Tetrahedron Letts. 1999, 40, 6149–6152.*
K. Doxsee et al., *J. Am. Chem. Soc. 111* (1989) 9129.
M. Jung et al., *J. Org. Chem. 56* (1991) 6729.
D. Dittmer et al., *J. Org. Chem. 37* (1972) 1111.

* cited by examiner

Primary Examiner—D. R. Wilson
Assistant Examiner—Rip Lee
(74) Attorney, Agent, or Firm—Jonathan L. Schuchardt; John Tyrell

(57) ABSTRACT

A single-site olefin polymerization catalyst and method of making it are disclosed. The catalyst comprises an activator and an organometallic complex. The complex comprises a Group 3 to 10 transition metal, M, and at least one anionic heterocyclobutenyl ligand that is bonded to M. Molecular modeling results indicate that single-site catalysts based on anionic heterocyclobutenyl ligands will have advantages compared with the performance of catalysts based on cyclopentadienyl and substituted cyclopentadienyl ligands.

18 Claims, No Drawings

COMPLEXES BASED ON FOUR-MEMBERED CYCLIC ANIONIC SIX-ELECTRON-DONOR LIGANDS

FIELD OF THE INVENTION

The invention relates to catalysts useful for olefin polymerization. In particular, the invention relates to "single-site" catalysts that incorporate at least one anionic heterocyclobutenyl ligand.

BACKGROUND OF THE INVENTION

Interest in single-site (metallocene and non-metallocene) catalysts continues to grow rapidly in the polyolefin industry. These catalysts are more reactive than Ziegler-Natta catalysts, and they produce polymers with improved physical properties. The improved properties include narrow molecular weight distribution, reduced low molecular weight extractables, enhanced incorporation of a-olefin comonomers, lower polymer density, controlled content and distribution of long-chain branching, and modified melt rheology and relaxation characteristics.

Traditional metallocenes commonly include one or more cyclopentadienyl groups, but many other ligands have been used. Putting substituents on the cyclopentadienyl ring, for example, changes the geometry and electronic character of the active site. Thus, a catalyst structure can be fine-tuned to give polymers with desirable properties. Other known single-site catalysts replace cyclopentadienyl groups with one or more heteroatomic ring ligands such as boraaryl (see, e.g., U.S. Pat. No. 5,554,775), pyrrolyl, indolyl, (U.S. Pat. No. 5,539,124), or azaborolinyl groups (U.S. Pat. No. 5,902,866).

Single-site catalysts typically feature at least one polymerization-stable, anionic ligand that is purely aromatic, as in a cyclopentadienyl system. All five carbons in the planar cyclopentadienyl ring participate in bonding to the metal in η-5 fashion. The cyclopentadienyl anion functions as a 6π-electron donor. Similar bonding apparently occurs with heteroatomic ligands such as boratabenzenyl or azaborolinyl.

In contrast, olefin polymerization catalysts that contain heterocyclobutenyl ligands are not known. The neutral ligand precursors can be prepared by known literature procedures.

In spite of the availability of synthetic routes to heterocyclobutenyl anions, their use as ligands for metallocene or single-site catalysts for olefin polymerization has not been suggested. Organometallic complexes from these ligands would provide a new class of potentially valuable catalysts to polyolefin producers.

SUMMARY OF THE INVENTION

The invention is a single-site olefin polymerization catalyst. The catalyst comprises an activator and an organometallic complex. The organometallic complex comprises a Group 3 to 10 transition metal, M, and at least one anionic heterocyclobutenyl ligand that is bonded to M.

Evidence from molecular modeling studies indicates that single-site catalysts based on anionic heterocyclobutenyl ligands will exhibit improved stability versus catalysts based on cyclopentadienyl and substituted cyclopentadienyl ligands. This improved stability should impart increased catalyst efficiency, especially at higher process temperatures.

Also provided is a two-step method of producing the catalyst. Step one involves deprotonating a heterocyclobutene and reacting the resulting anion with a Group 3 to 10 transition metal source to produce an organometallic complex comprising the metal, M, and at least one heterocyclobutenyl ligand that is bonded to M. In step two, the product is combined with an activator. The ease and inherent flexibility of the synthesis puts polyolefin makers in charge of a new family of single-site catalysts.

DETAILED DESCRIPTION OF THE INVENTION

Catalysts of the invention comprise an activator and an organometallic complex. The catalysts are probably "single site" in nature, i.e., they are distinct chemical species rather than mixtures of different species. They should give polyolefins with characteristically narrow molecular weight distributions (Mw/Mn<3) and good, uniform comonomer incorporation.

The organometallic complex includes a Group 3 to 10 transition metal, M. As used herein, "transition metal" includes metals of the lanthanide and actinide series. More preferred complexes include a Group 4 to 6 transition metal; most preferably, the complex contains a Group 4 metal, i.e., titanium, zirconium or hafnium.

The organometallic complex also comprises at least one heterocyclobutenyl anion that is bonded, most likely π-bonded, to the metal. By "heterocyclobutenyl anion," we mean an anion formed from a four-membered cyclobutene ring where one of the saturated carbons in the cyclobutene is replaced with a heteroatom.

The heterocyclobutenyl anions are usually generated from the corresponding neutral compounds by deprotonation with a potent base as is described in more detail below. The synthesis of phosphacyclobutenes (dihydrophosphetes) from the corresponding titanacyclobutene is known (see K. Doxsee et al., J. Am. Chem. Soc. 111 (1989) 9129), and azacyclobutenes (azetines) should be available from the same method. Alternatively, azetines should be available from a method analogous to that described in the literature for 1-acyl-2-azetines (see M. Jung et al., J. Org. Chem. 56 (1991) 6729), where an azetidonol is mesylated, and then the mesylate is treated with base to eliminate methanesulfonic acid and afford the azetine. The synthesis of thiacyclobutenes (thietes) by facile Hofmann elimination of the 3-aminothietane derivatives has been described (see D. Ditmer et al., J. Org. Chem. 37 (1972) 1111). The chemistry of oxetenes has been reviewed (see R. Linderman, Compr. Heterocycl. Chem. II (1996), 1B 721–753, Editor A. Padwa, Elsevier Publishers Oxford, UK).

The heterocyclobutenyl anion may be bridged to another ligand, which may or may not be another heterocyclobutenyl anion. Preferred heterocyclobutenyl anions have the general structure:

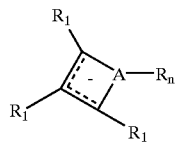

where A is N, P, O or S. R is $C_1$–$C_{30}$ hydrocarbyl or trialkylsilyl. When A is N or P, n is 1; when A is O or S, n is 0; each $R_1$ is independently selected from the group consisting of R, H, Cl, and Br. When A is N, the anion is said to be an azetinyl anion. When A is P, the anion is said to be a phosphetyl anion. When A is S, the anion is said to be a thietyl anion and when A is O, the anion is an oxetenyl anion.

Exemplary anions are:

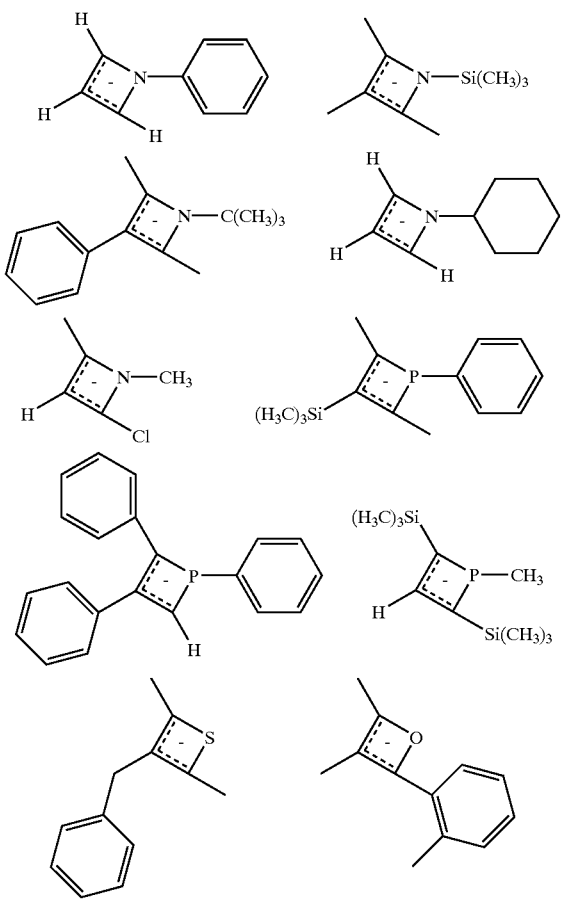

The organometallic complex optionally includes one or more additional polymerization-stable, anionic ligands. Examples include substituted and unsubstituted cyclopentadienyl, fluorenyl, and indenyl, or the like, such as those described in U.S. Pat. Nos. 4,791,180 and 4,752,597, the teachings of which are incorporated herein by reference. A preferred group of polymerization-stable ligands are heteroatomic ligands such as boraaryl, pyrrolyl, indolyl, indenoindolyl, quinolinoxy, pyridinoxy, and azaborolinyl as described in U.S. Pat. Nos. 5,554,775, 5,539,124, 5,637,660, 5,902,866 and 6,232,260, the teachings of which are incorporated herein by reference. The organometallic complex also usually includes one or more labile ligands such as halides, alkyls, alkaryls, aryls, dialkylaminos, or the like. Particularly preferred are halides, alkyls, and alkaryls (e.g., chloride, methyl, benzyl).

The heterocyclobutenyl anions and/or polymerization-stable ligands can be bridged. For instance, a —CH$_2$—, —CH$_2$CH$_2$—, or (CH$_3$)$_2$Si bridge can be used to link two heterocyclobutenyl anions or a heterocyclobutenyl anion and a polymerization-stable ligand. Groups that can be used to bridge the ligands include, for example, methylene, ethylene, 1,2-phenylene, and dialkyl silyls. Normally, only a single bridge is included. Bridging changes the geometry around the transition metal and can improve catalyst activity and other properties such as comonomer incorporation.

The organometallic complex preferably has the general structure:

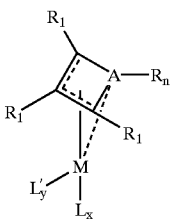

where M is a transition metal and A is N, P, O or S. R is C$_1$–C$_{30}$ hydrocarbyl or trialkylsilyl. When A is N or P, n is 1; when A is O or S, n is 0; each R$_1$ is independently selected from the group consisting of R, H, Cl, and Br. Each L is independently halide, alkoxy, siloxy, alkylamino or C$_1$–C$_{30}$ hydrocarbyl. L' is substituted or unsubstituted cyclopentadienyl, indenyl, fluorenyl, boraaryl, pyrrolyl, indolyl, indenoindolyl, quinolinoxy, pyridinoxy or azaborolinyl; y is 0 or 1; and x+y satisfies the valence of M.

The catalysts include an activator. Suitable activators ionize the organometallic complex to produce an active olefin polymerization catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis (pentafluorophenyl)borate, lithium tetrakis (pentafluorophenyl)aluminate, anilinium tetrakis (pentafluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference.

Suitable activators also include aluminoboronates—reaction products of alkyl aluminum compounds and organoboronic acids—as described in U.S. Pat. Nos. 5,414,180 and 5,648,440, the teachings of which are incorporated herein by reference.

The amount of activator needed relative to the amount of organometallic complex depends on many factors, including the nature of the complex and activator, the desired reaction rate, the kind of polyolefin product, the reaction conditions, and other factors. Generally, however, when the activator is an alumoxane or an alkyl aluminum compound, the amount used will be within the range of about 0.01 to about 5000 moles, preferably from about 0.1 to about 500 moles, of aluminum per mole of M. When the activator is an organoborane or an ionic borate or aluminate, the amount used will be within the range of about 0.01 to about 5000 moles, preferably from about 0.1 to about 500 moles, of activator per mole of M.

The activator is normally added to the reaction mixture at the start of the polymerization. However, when a supported catalyst system is used, the activator can be deposited onto the support along with the organometallic complex.

The catalyst systems are optionally used with an inorganic solid or organic polymer support. Suitable supports include silica, alumina, silica-aluminas, magnesia, titania, clays, zeolites, or the like. The support is preferably treated thermally, chemically, or both prior to use to reduce the concentration of surface hydroxyl groups. Thermal treatment consists of heating (or "calcining") the support in a dry atmosphere at elevated temperature, preferably greater than about 100° C., and more preferably from about 150° C. to about 600° C., prior to use. A variety of different chemical treatments can be used, including reaction with organoaluminum, -magnesium, -silicon, or -boron compounds. See, for example, the techniques described in U.S. Pat. No. 6,211,311, the teachings of which are incorporated herein by reference.

The complex and activator can be deposited on the support in any desired manner. For instance, the components can be dissolved in a solvent, combined with a support, and stripped. Alternatively, an incipient-wetness technique can be used. Moreover, the support can simply be introduced into the reactor separately from the complex and activator.

The loading of complex on the support varies depending upon a number of factors, including the identities of the complex and the support, the type of olefin polymerization process used, the reaction conditions, and other concerns. Usually, the amount of complex used is within the range of about 0.01 to about 10 wt. % of transition metal based on the amount of supported catalyst. A more preferred range is from about 0.1 to about 4 wt. %.

The invention includes a method for making the organometallic complex. The method comprises deprotonating a heterocyclobutene with at least one equivalent of a potent base such as lithium diisopropylamide, n-butyllithium, sodium hydride, a Grignard reagent, a combination of n-butyllithium and potassium t-butoxide or the like. The resulting anion is reacted with a Group 3 to 10 transition metal source to produce an organometallic complex. The complex comprises the metal, M, and at least one heterocyclobutenyl anionic ligand that is bonded, and probably π-bonded, to the metal. Any convenient source of the Group 3 to 10 transition metal can be used. Usually, the source is a complex that contains one or more labile ligands that are easily displaced by the heterocyclobutenyl anion. Examples are halides (e.g., $TiCl_4$, $ZrCl_4$), alkoxides, amides, and the like. The metal source can incorporate one or more of the polymerization-stable anionic ligands described earlier. The organometallic complex can be used "as is." Often, however, the complex is converted to an alkyl derivative by treating it with an alkylating agent such as methyllithium. The alkylated complexes are more suitable for use with certain activators (e.g., ionic borates).

The heterocyclobutenyl anion is preferably generated at low temperature (0° C. to 100° C.), preferably in an inert solvent (e.g., a hydrocarbon or ether). The anion is then usually added to a solution of the transition metal source at low to room temperature. After the reaction is complete, by-products and solvents are removed to give the desired transition metal complex.

In another approach to making the complex, a synthetic equivalent of a heterocyclobutenyl anion reacts with the Group 3–10 transition metal source. By "synthetic equivalent," we mean a neutral compound capable of generating an anionic heterocyclobutenyl ligand under the reaction conditions. Suitable synthetic equivalents include heterocyclobutenes that are C-substituted with $—QR''_3$ groups, where Q is Si, Sn, or Ge, and R" is a $C_1$–$C_{30}$ hydrocarbyl group. When combined with suitable transition metal sources, particularly ones that have a labile anionic group such as halide or dialkylamino, a complex incorporating a heterocyclobutenyl anion is produced with elimination of a neutral Sn, Ge, or Si-containing by-product. Usually, it suffices to combine the synthetic equivalent and the transition metal source in a suitable solvent and heat if needed to complete the reaction. For example:

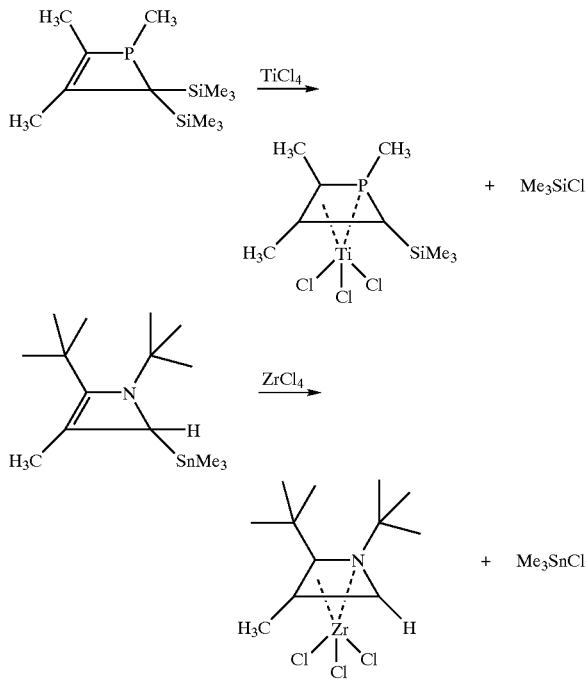

The catalysts are particularly valuable for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes. Suitable methods for polymerizing olefins using the catalysts of the invention are described, for example, in U.S. Pat. Nos. 5,902,866, 5,637,659, and 5,539,124, the teachings of which are incorporated herein by reference.

The olefin polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 15 psia to about 50,000 psia. More preferred is the range from about 15 psia to about 1000 psia.

Catalyst concentrations used for the olefin polymerization depend on many factors. Preferably, however, the concentration ranges from about 0.01 micromoles per liter to about 100 micromoles per liter. Polymerization times depend on the type of process, the catalyst concentration, and other factors. Generally, polymerizations are complete within several seconds to several hours.

The following examples merely illustrate the invention. Those skilled in the art will recognize many variations that are within the spirit of the invention and scope of the claims.

EXAMPLE 1

Triphenylphosphete (structure below) is prepared by the method Doxsee et al. (*J. Am. Chem. Soc.* 111 (1989) 9129).

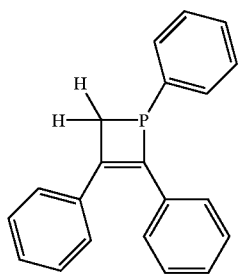

n-Butyllithium (2.0 mL of 1M hexane solution, 2 mmol) is added to a solution of tetrahydrofuran containing 20 mL tetrahydrofuran and 2.0 mL of 1M potassium t-butoxide in tetrahydrofuran. This mixture is stirred 2 hours and a solution of 600 mg (2 mmol) of triphenylphosphete in 30 mL tetrahydrofuran is added. The mixture is stirred for an additional 2 hours and solvent removed in vacuo. The residue is extracted with hexane to remove the lithium t-butoxide. To the extracted residue, 30 mL of tetrahydrofuran is added. After stirring, it is then added via cannula to a stirring mixture of 525 mg (2 mmol) of cyclopentadienylzirconium trichloride in tetrahydrofuran. The mixture is stirred 6 hours at room temperature and volatiles removed in vacuo. The residue is extracted with toluene to give a solution of the organometallic complex. This solution can be used "as is" for polymerizing olefins. The expected product is triphenylphosphetyl-(cyclopentadienyl)zirconium dichloride.

EXAMPLE 2

Ethylene Polymerization

A one-liter, stainless-steel reactor is charged with toluene (500 mL) and polymethalumoxane (2.2 mL of 4.14 M solution of PMAO in toluene, Al/Ti=2000). The reactor is charged with ethylene to 350 psig, and the contents are heated to 70° C. An aliquot of the toluene solution of the triphenylphosphetyl(cyclopentadienyl)zirconium dichloride (containing 1.0 mg of complex) from Example 1 is injected into the reactor to start the polymerization. Ethylene is supplied on demand to keep the reactor pressure constant at 350 psig. After about 1 hour, the reactor is vented to recover polyethylene as the expected product.

MOLECULAR MODELING STUDY

Additional evidence for the suitability of heterocyclobutenyl anions as ligands for single-site catalysts comes from molecular modeling studies. All calculations have been performed with complete geometry optimization using the DFT model B3LYP with the LACVP** pseudopotential basis set as incorporated into the TITAN™ software package.

The relative acidity of anion precursor carbon acids (toluene, cyclobutene and aza-cyclobutene) were estimated relative to the acidity of cyclopentadiene by comparing the enthalpies (ΔΔH) of the model reactions:

$$XC-H + Cp^- \rightarrow XC^- + CpH$$

where

XC—H is the carbon acid precursor,
Cp- is the cyclopentadienyl anion,

XC— is the anionic ligand precursor and

CpH is cyclopentadiene.

Based on these estimates, azacyclobutene (ΔΔH=7.3 kcal/mole) is more acidic than either toluene (ΔΔH=28.0 kcal/mole) or cyclobutene (ΔΔH=57.1 kcal/mole). Thus, the routinely used deprotonating agents (e.g., alkyl-lithium or alkyl-potassium compounds) are basic enough to generate the corresponding azetinyl anion.

To estimate the effect of ligands (L and L') on the relative stability of the zirconocenium active sites, we are using the relative enthalpy (ΔΔH$_f$) of the reaction:

$$LL'ZrMe_2 \rightarrow LL'ZrMe^+ + Me^-$$

compared with the enthalpy of a standard process in which the zirconium is bonded to two cyclopentadienyl ligands:

$$Cp_2ZrMe_2 \rightarrow Cp_2ZrMe^+ + Me^-$$

According to these estimates (Table 1), the azetinyl ligand should stabilize an electrophilic active site more effectively compared with a cyclopentadienyl ligand and similarly to an indenyl or fluorenyl ligand.

TABLE 1

| Complex | ΔΔH$_f$, kcal/mole |
|---|---|
| Cp$_2$ZrMe$_2$ | 0 |
| (Ind)(Cp)ZrMe$_2$ | −6.9 |
| (Flu)(Cp)ZrMe$_2$ | −10.4 |
| (N-Me-azetinyl)(Cp)ZrMe$_2$ | −9.0 |

The increased stability of the active site for the N-methylazetinyl complex permits a high concentration of active sites in the polymerization process, which results in a more active catalyst.

Remarkably, the increased stability of the zirconocenium cation with the azetinyl ligand results only in a minor reduction (2.2 kcal/mole) in its reactivity toward ethylene as characterized by the calculated heat of pi-complexation as compared to the bis-cyclopentadienyl zirconocenium ion (Table 2).

TABLE 2

| Active site | Relative heat of interaction of active site with ethylene, kcal/mol |
|---|---|
| Cp$_2$ZrMe+ | 0 |
| (Ind)(Cp)ZrMe+ | 3.6 |
| (Flu)(Cp)ZrMe+ | 4.2 |
| (N-Me-azetinyl)(Cp)ZrMe+ | 2.2 |

Further calculations were done to compare the $E_a$ for ethylene isertion.

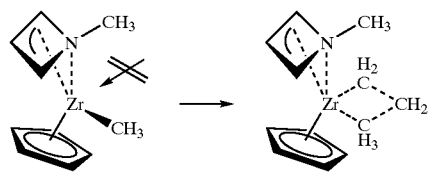

$E_a$ = 7.1 kcal/mole

-continued

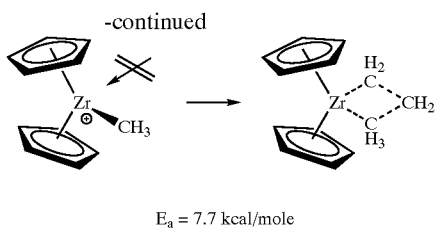

$E_a = 7.7$ kcal/mole

These calculations show a similar or perhaps slightly better (lower) activation energy for ethylene insertion The preceding examples are meant only as illustrations. The following claims define the invention.

I claim:

1. A catalyst which comprises:
   (a) an activator; and
   (b) an organometallic complex comprising a Group 3 to 10 transition metal, M, and at least one anionic heterocyclobutenyl ligand that is bonded to M.

2. The catalyst of claim 1 wherein the activator is selected from the group consisting of alumoxanes, alkylaluminum compounds, organoboranes, ionic borates, ionic aluminates and aluminoboronates.

3. The catalyst of claim 1 comprising a Group 4 transition metal.

4. The catalyst of claim 1 further comprising a substituted or unsubstituted cyclopentadienyl, indenyl, or fluorenyl group.

5. The catalyst of claim 1 further comprising a polymerization-stable, anionic ligand selected from the group consisting of boraaryl, pyrrolyl, indolyl, indenoindolyl, quinolinoxy, pyridinoxy, and azaborolinyl.

6. The catalyst of claim 1 wherein the heterocyclobutenyl ligand is bridged to another ligand.

7. The catalyst of claim 6 wherein the heterocyclobutenyl ligand is bridged to another heterocyclobutenyl ligand.

8. The catalyst of claim 1 wherein the heterocyclobutenyl ligand is a 2-azetinyl ligand.

9. The catalyst of claim 1 wherein the heterocyclobutenyl ligand is a 2-phosphetyl ligand.

10. The catalyst of claim 1 wherein the heterocyclobutenyl ligand has the structure:

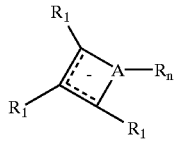

in which A is selected from the group consisting of N, P, O and S; R is selected from the group consisting of $C_1$–$C_{30}$ hydrocarbyl and trialkylsilyl; when A is N or P, n is 1; when A is O or S, n is 0; and each $R_1$ is independently selected from the group consisting of R, H, Cl, and Br.

11. The catalyst of claim 1 wherein the complex has the structure:

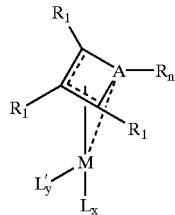

wherein M is a Group 3 to 10 transition metal; A is selected from the group consisting of N, P, O and S; R is selected from the group consisting Of $C_1$–$C_{30}$ hydrocarbyl and trialkylsilyl; when A is N or P, n is 1; when A is O or S, n is 0; each $R_1$ is independently selected from the group consisting of R, H, Cl, and Br; each L is independently selected from the group consisting of halide, alkoxy, siloxy, alkylamino and $C_1$–$C_{30}$ hydrocarbyl; L' is selected from the group consisting of substituted or unsubstituted cyclopentadienyl, indenyl, fluorenyl, boraarl, pyrrolyl, indolyl, indenoindolyl, quinolinoxy, pyridinoxy, and azaborolinyl; y is 0 or 1; and x+y satisfies the valence of M.

12. The catalyst of claim 11 wherein L or L' is covalently bonded to the heterocyclobutenyl ligand.

13. A method of producing the catalyst of claim 1 which comprises:
   (a) deprotonating a heterocyclobutene and reacting the resulting anion with a Group 3 to 10 transition metal source to produce an organometallic complex comprising the metal, M, and at least one heterocyclobutenyl ligand that is bonded to M, and
   (b) combining the product of (a) with an activator.

14. A supported catalyst of claim 1.

15. A process which comprises polymerizing an olefin in the presence of the catalyst of claim 1.

16. A process which comprises copolymerizing ethylene with a $C_3$–$C_{10}$ alpha-olefin in the presence of the catalyst of claim 1.

17. A method which comprises reacting a synthetic equivalent of a heterocyclobutenyl anion with a Group 3 to 10 transition metal source to produce an organometallic complex comprising the metal, M, and at least one heterocyclobutenyl ligand that is bonded to M.

18. The method of claim 17 wherein the synthetic equivalent has the structure:

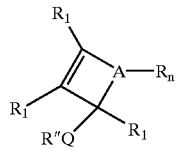

in which A is selected from the group consisting of N, P, O and S; R is selected from the group consisting of $C_1$–$C_{30}$ hydrocarbyl and trialkylsilyl; when A is N or P, n is 1; when A is O or S, n is 0; each $R_1$ is independently selected from the group consisting of R, H, Cl, and Br; Q is selected from the group consisting of Si, Sn and Ge; and R" is a $C_1$–$C_{30}$ hydrocarbyl group.

* * * * *